(12) United States Patent
Canonaco et al.

(10) Patent No.: US 7,998,142 B2
(45) Date of Patent: Aug. 16, 2011

(54) NAVIGATED LATERAL/MEDIAL FEMORAL RESECTION GUIDE

(75) Inventors: Alex F. Canonaco, Caldwell, NJ (US);
Michael J. Cusick, Collierville, TN (US); Sandeep K. Chauhan, Plumpton Green (GB)

(73) Assignee: Howmedica Osteonics Corp., Mahwah, NJ (US)

( * ) Notice: Subject to any disclaimer, the term of this patent is extended or adjusted under 35 U.S.C. 154(b) by 1114 days.

(21) Appl. No.: 11/653,160

(22) Filed: Jan. 12, 2007

(65) Prior Publication Data

US 2007/0123900 A1    May 31, 2007

Related U.S. Application Data

(62) Division of application No. 10/849,625, filed on May 19, 2004, now Pat. No. 7,182,767.

(51) Int. Cl.
*A61F 2/00* (2006.01)
(52) U.S. Cl. .................................................. 606/89
(58) Field of Classification Search .............. 606/86 R, 606/87, 88, 89
See application file for complete search history.

(56) References Cited

U.S. PATENT DOCUMENTS

| | | | |
|---|---|---|---|
| 5,122,144 A | 6/1992 | Bert et al. | |
| 5,514,139 A | 5/1996 | Goldstein | |
| 5,569,261 A * | 10/1996 | Marik et al. | 606/88 |
| 5,597,379 A | 1/1997 | Haines et al. | |
| 5,601,563 A | 2/1997 | Burke et al. | |
| 5,643,272 A | 7/1997 | Haines | |
| 5,709,689 A * | 1/1998 | Ferrante et al. | 606/86 R |
| 5,755,803 A | 5/1998 | Haines et al. | |
| 5,769,855 A | 6/1998 | Bertin et al. | |
| 5,810,827 A | 9/1998 | Haines | |
| 5,879,354 A | 3/1999 | Haines et al. | |

(Continued)

FOREIGN PATENT DOCUMENTS

CA    2 255 041    11/1997

(Continued)

OTHER PUBLICATIONS

Biomedical Engineering Trust, South Orange, NJ, 1994, NJ LCS®, Unicompartmental Knee System with Porocoat®, Surgical Procedure by Frederick F. Buechel, M.D.

(Continued)

*Primary Examiner* — Thomas C Barrett
*Assistant Examiner* — Christopher Beccia
(74) *Attorney, Agent, or Firm* — Lerner, David, Littenberg, Krumholz & Mentlik, LLP

(57) ABSTRACT

A multi-piece knee resection instrument for use in forming an anterior cut, an anterior chamfer cut, a posterior cut and a posterior chamfer cut on a distal femur which has already had a distal surface thereof resected which cuts are for the mounting of a prosthetic implant, has a first resection guide for attachment to the medial or lateral side of the distal femur. The first resection guide has a first surface facing generally anteriorly when mounted and a second surface extending distally from the first surface and angled thereto and a third surface extending generally parallel to the resected distal surface of the femur. A second resection guide is mounted on the first and second surfaces of the first resection guide for performing the anterior and anterior chamfer cuts. A third resection guide is mounted on the third surface of the first resection guide and extends in a medial-lateral direction therefrom across at least part of the resected distal femoral surface.

14 Claims, 6 Drawing Sheets

U.S. PATENT DOCUMENTS

| | | | |
|---|---|---|---|
| 5,935,128 | A | 8/1999 | Carter et al. |
| 6,056,754 | A | 5/2000 | Haines |
| 6,197,064 | B1 | 3/2001 | Haines et al. |
| 6,558,391 | B2 * | 5/2003 | Axelson et al. .................. 606/88 |
| 6,575,980 | B1 | 6/2003 | Robie et al. |
| 6,695,848 | B2 | 2/2004 | Haines |
| 6,702,821 | B2 | 3/2004 | Bonutti |
| 6,770,077 | B2 * | 8/2004 | Van Zile et al. ................. 606/88 |
| 6,780,190 | B2 | 8/2004 | Maroney |
| 7,182,767 | B2 * | 2/2007 | Canonaco et al. ............... 606/89 |
| 7,344,541 | B2 * | 3/2008 | Haines et al. ................... 606/88 |
| 7,572,262 | B1 * | 8/2009 | Hoeppner et al. ............... 606/88 |
| 2003/0018338 | A1 | 1/2003 | Axelson et al. |
| 2003/0171757 | A1 * | 9/2003 | Coon et al. ...................... 606/87 |
| 2004/0039395 | A1 | 2/2004 | Coon et al. |
| 2004/0039396 | A1 * | 2/2004 | Couture et al. ................. 606/87 |
| 2004/0260301 | A1 * | 12/2004 | Lionberger et al. ............. 606/88 |
| 2005/0190380 | A1 | 9/2005 | Plassky et al. |

FOREIGN PATENT DOCUMENTS

| | | |
|---|---|---|
| EP | 1 302 167 A | 4/2003 |
| WO | WO-96/07361 A | 3/1996 |
| WO | WO-98/53747 A | 12/1998 |

OTHER PUBLICATIONS

Partial European Search Report, EP 05 29 0775, Dated Sep. 6, 2005.

* cited by examiner

NAVIGATED LATERAL/MEDIAL FEMORAL RESECTION GUIDE

CROSS-REFERENCE TO RELATED APPLICATIONS

This application is a divisional of U.S. application Ser. No. 10/849,625, filed on May 19, 2004, the disclosure of which is incorporated herein by reference.

BACKGROUND OF THE INVENTION

This invention relates to the forming of bone cuts on a distal femur.

In particular, the application relates to forming an anterior bone cut, an anterior chamfer bone cut, a posterior bone cut and a posterior chamfer cut on a distal femur in which the distal bone cut has already been performed.

Total knee arthroplasty involves replacement of portions of the patella, femur and tibia with artificial components. In particular, a proximal portion of the tibia and a distal portion of the femur are cut away (resected) and replaced with artificial components. In performing this knee surgery, it has been desirable to minimize the size of the incision to thereby minimize damage to soft tissue.

In particular, it is necessary to resect the proximal tibia and distal femur with, among other cuts, a facing pair of planar cuts from which other bone cuts, in the case of the femur, can be referenced.

In order to make these cuts, resecting the femur and tibia necessitated significant cutting of soft tissue, including muscles, tendons and ligaments.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

There are several types of knee prosthesis known in the art. One type is sometimes referred to as a "resurfacing type." In these prostheses, the articular surface of the distal femur and the proximal tibia are "resurfaced" with respective metal and plastic condylar-type articular bearing components. Preferably, these components are made of titanium alloy or a cobalt-chrome alloy such as VITALLIUM® alloy.

One important aspect of these procedures is the correct resection of the distal femur and proximal tibia. These resections must provide planes which are correctly angled in order to properly accept and align the prosthetic components. In particular, the resection planes on the tibia and femur must be correctly located relative to at least three parameters: proximal-distal location; varus-valgus angle; and flexion-extension angle.

Moreover, following distal resection, the femur must be further shaped with the aid of a cutting block, the cutting block must be correctly located relative to internal-external rotation, medial-lateral position and anterior-posterior position. Recently, various computerized systems have been introduced to aid the practitioner during different surgical procedures. These systems improve accuracy of the cuts based on accurately locating the mechanical axis of the tibia and femur and provides the ability to verify the cuts made. In these systems, there is utilized multiple video cameras which are deployed above the surgical site and a plurality of dynamic reference frame devices also known as trackers. These trackers are attached to body parts and the surgical instruments and preferably include light emitting devices, such as light emitting diodes which are visible to the video cameras. Using software designed for a particular surgical procedure, a computer receiving input from the camera guides the placements of the surgical instruments with respect to landmarks on the body. Such systems are shown in U.S. Pat. Nos. 6,385,475 and 6,514,259, the teachings of which are incorporated herein by reference.

In co-pending application, Ser. No. 10/768,520 assigned to the assignee of the present invention, an instrument for resecting the distal facing surface of the femur from the medial or lateral side is provided. It is desirable to have a cutting block system which can be attached on the medial or lateral side of the femur for performing the other four bone cuts on the distal femur. It is particularly advantageous to have a multi-piece, preferably, a three piece cutting block, which pieces can be assembled in a manner so that it can be mounted on the medial or lateral side of the right or left knee and still be able to make the four bone cuts.

The instrumentation of the present invention includes components for resecting four of the bone cuts on the distal femur and includes an alignment system for properly positioning the cutting guide surfaces utilizing an optical tracking system optically coupled to a computer system. The design of the multi-piece instruments of the present invention allows the resection of the distal end to be performed anteriorly-laterally as contrasted with the typical resection systems of the prior art in which the resections are all performed from the anterior direction.

U.S. Patent Publication No. 2003/0171757 relates to an instrument that permits resection of the proximal end of the tibia and distal end of the femur to be performed either medially or laterally.

SUMMARY OF THE INVENTION

The invention relates to a multi-piece cutting system and method of forming the anterior, anterior chamfer, posterior and posterior chamfer cuts on a distal femur utilizing optical tracking systems and computer-aided surgery. The system preferably includes five separate pieces, two of which are used only when aligning the resection guide block on the distal femur. One of these pieces is an anterior positioning arm which mounts on a portion of the resection guide block surface of the femur to set the anterior/posterior location on the distal femur. The second piece used on the block is a removable optical tracker mount. The tracker preferably includes at least three light emitting diodes so that the plane where the cut to be made can be determined by the computer system via video camera inputs. Use of the tracker allows the surgeon to orient the cutting block free-handedly adjacent the medial or lateral bone of the distal femur and align the cutting surface in the correct internal/external rotational alignment. By free-hand it is meant that without extramedullary alignment or intramedullary alignment. Once the proper positioning has occurred, the surgeon then inserts bone pins through the resection guide block into the femur.

It is an object of the invention to provide a multi-piece resection guide system for use in performing the anterior, anterior chamfer, posterior and posterior chamfer bone cuts on a distal femur.

It is yet an additional object of the invention to provide a resection guide system which includes pieces which can assembled in a manner allowing the mounting of the guide block on either the medial or lateral of either the left or right knee.

It is still an additional object of the invention to provide a guide block which allows for the modular mounting of an anterior referencing arm, an optical tracker adapter for use with an optical tracking device of a navigated instrument system and a modular cutting guide for use in performing the anterior and anterior chamfer bone cuts.

These and other objects of the invention are achieved by a multi-piece knee resection instrument for resecting the distal femur which has a first resection guide for attachment to the medial or lateral side of the distal femur, which guide has a first surface facing generally anteriorly when mounted and a second surface extending distally from the first surface at an angle thereto and a third surface extending generally parallel to the distal surface of the resected femur. The first and second surfaces can be used to guide a saw blade, however, in the preferred embodiment, a second resection guide is mounted on the first and second surfaces, the guide including a slot for receiving a saw blade of a powered oscillating saw. The instrument also includes a third resection guide mounted on the third surface of the first resection guide and extending in a medial-lateral direction therefrom across at least part of the distal surface of the femur. The second resection guide can be mounted on both the first surface of the first resection guide and the second surface for making the anterior and anterior chamfer cuts on the femur respectively.

The multi-piece resection instrument further includes an anterior referencing guide for selective mounting on the first surface of the first resection guide and also includes an optical tracker mountable on the first resection guide in any trackable position. Preferably, the optical tracker is mounted on the first surface of the first resection guide. However, as long as the optics of the navigation system can view the optical tracker on the first resection, it can be mounted in any position thereon. Preferably, the anterior referencing guide includes an arm extending in a medial-lateral direction for contacting the anterior surface of the distal femur.

The third resection guide has a first saw guide slot for resecting a posterior surface of the distal femur and a second saw guide slot extending in an anterior/posterior direction along a plane angled with respect to the coronal plane for making a posterior chamfer cut on the distal femur. Both the first and third resection guides include a plurality of bores extending towards the bone for receiving bone pins for mounting the first and second guides on the femur.

The multi-piece instruments may be supplied as part of a kit in which the first portion of the resection guide block and the second portion of the resection guide block come in various sizes for use with different size femurs. Generally, there are seven different sizes provided. A plurality of separate cutting guides are provided for making the anterior and anterior chamfer cut, however, such cutting guides, which are mounted on the first resection block portion may also be of the same size, although it is possible to have longer guides for larger distal femurs. Likewise, the modular tracker and anterior referencing arm which are mounted on the resection block first portion may be of the same size for all of the different size first and second portions provided. Preferably, the first and second portion are coupled together by a post on the first portion extending to a bore on the second portion which can then be locked via a set screw extending through a bore which intersects the bore of the second portion and therefore can engage the post of the first portion.

A method for using the cutting block to make the anterior bone cut, the anterior chamfer bone cut, the posterior bone cut and the posterior chamfer bone cut is also disclosed. Initially, the distal femur is resected in a typical manner to form a planar distal surface. Then a first portion of the resection guide block of the present invention is located adjacent either the medial or lateral side of the distal femur. The resection guide block is located in the anterior/posterior direction by contacting an anterior surface of the distal femur with an anterior referencing arm mounted on the resection guide block. The resection guide block has a medial-laterally extending second portion having a surface for contacting the resected distal femur and includes saw guide slots for making the posterior bone cut and the posterior chamfer bone cut. The resection guide block is oriented in the anterior/posterior direction and in internal/external rotation and thereafter pinned to the femur. The anterior bone cut is made by guiding a saw blade on a first surface of the resection guide block first portion and performing the anterior chamfer cut with a saw blade guided on a second surface of the resection guide block first portion and performing the posterior and posterior chamfer cuts with the second portion of the cutting block.

The method can further include the placement of a modular cutting guide on the first and second surfaces of the first portion performed the anterior and anterior chamfer cuts. In accomplishing this, the saw blade may be oriented at an oblique angle, i.e. anterior-lateral or anterior-medial rather than a pure anterior approach.

In the preferred embodiment, the first portion of the resection guide has a distally extending coupling element and a second portion has a coupling element engageable with the first portion coupling element to form the resection guide block. The second portion includes a coupling element adjacent each end so that the first and second portions may be assembled in a manner that provides a resection guide block for the right knee with a medial side approach or a lateral side approach for the left knee and engaging the second end of the second portion with the first portion coupling forms a cutting block for the left knee for the medial side or the lateral side of the right knee.

While the anterior/posterior location of the guide block is performed with the anterior referencing arm, the internal/external rotation is set with an optical tracker mounted preferably on the first portion of the resection guide block.

When a modular cutting guide is used it may be placed on an anteriorly facing surface of the resection guide to perform the anterior cut and may be removed from that surface and placed on a sloping surface to perform the anterior chamfer cut. Prior to placing the modular cutting guide on the resection guide block first surface, both the optical tracker and the anterior referencing instrument are removed.

BRIEF DESCRIPTION OF THE DRAWINGS

The present invention will be better understood on reading the following detailed description of non-limiting embodiments thereof, and on examining the accompanying drawings, in which:

FIG. 7a is a cross-sectional view of the cutting guide along lines 7a-7a;

DETAILED DESCRIPTION

Figure 1:
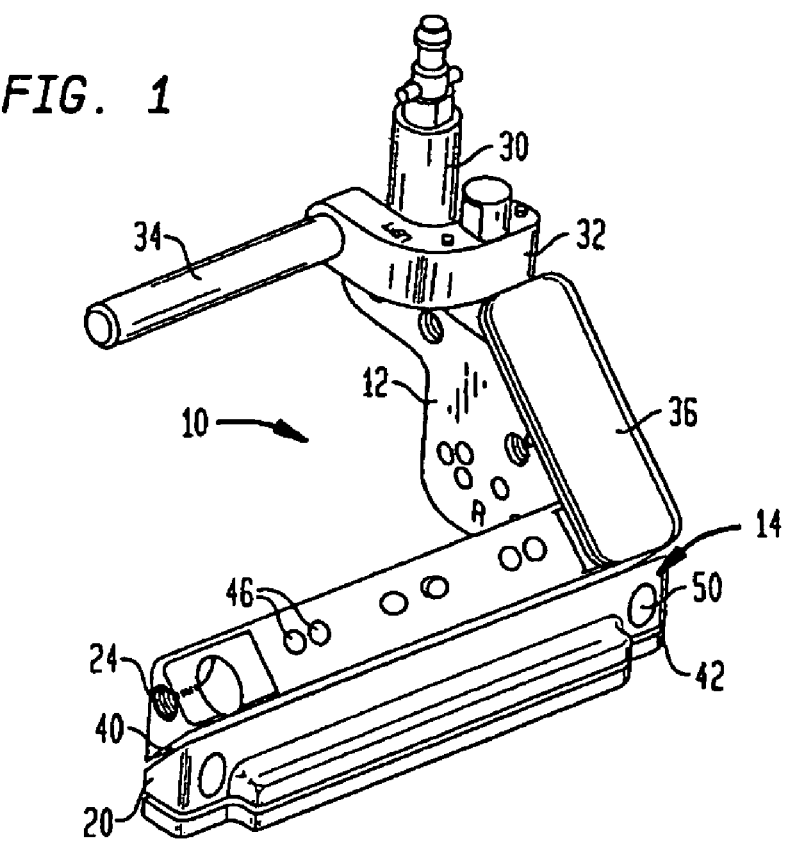
FIG. 1 is a perspective view of the multi-piece femoral resection guide of the present invention with the tracker mount and an anterior referencing guide mounted thereon.
Figure 2:
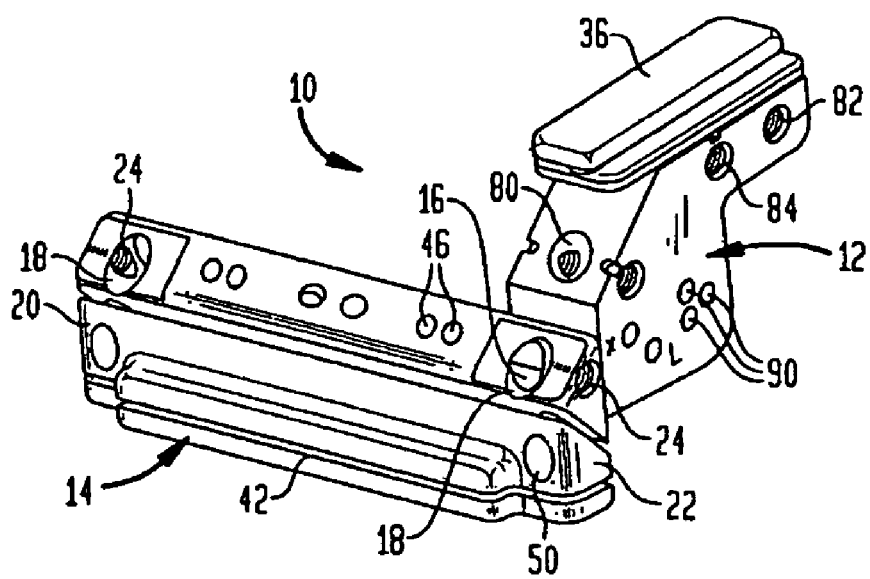
FIG. 2 is a perspective view of the cutting guide of FIG. 1 with the optical tracker mounting anterior referencing guide removed with the modular cutting guide located on a surface thereof adapted to cut the anterior surface of the femur.

Referring to FIGS. 1 and 2, there is shown a perspective view of the multi-piece femoral resection system of the present invention generally denoted as 10. Resection system 10 includes a resection guide block having a first portion 12 which is adapted to be mounted on the medial or lateral side of the femur in a manner as will be discussed below. The resection guide block has a second portion 14 which is coupled to first portion 12, in the preferred embodiment, by a coupling element 16 which, in the preferred embodiment, is an outwardly extending post 16 which is integral with first portion 12 and extends through a bore 18 formed in the second portion 14. In the preferred embodiment, there is a bore 18 adjacent both a first end 20 and a second end 22 of second portion 14. Having two bores allows first portion 12 to be mounted adjacent to either end 20 or end 22 of second portion 14 depending on whether the resection system is used on the right or left knee or placed medially or laterally on the femur. In the preferred embodiment, post 16 is held within bore 18 by a set screw (not shown) which extends into a pair of bores 24, one located on side 20 and one side 22 of second portion 14.

As can be best seen in FIG. 1, system 10 further includes a post 30 which is adapted for mounting an optical tracker which is well known in the art. System 10 also includes an anterior referencing guide 32 which can be attached to first portion 12 and includes an arm 34 for engaging the anterior surface of the femur to assist in locating the cutting block in the anterior/posterior direction on the distal femur. In the preferred embodiment, system 10 further includes a resection guide 36 which can be mounted on first portion 12 and is positionable to assist in cutting the anterior and anterior chamfer bone cuts on the distal femur. Referring to FIG. 2 cutting guide 36 is positioned on an anteriorly facing surface of first portion 12 and is thus positioned for performing an anterior cut on the femur. In FIG. 1, cutting guide 36 is placed on an angled or sloping surface angled with respect to the anteriorly facing surface of block 12 and the distal surface of second portion 14 and is thus in a position to make the anterior chamfer cut on the distal femur.

Figure 3:
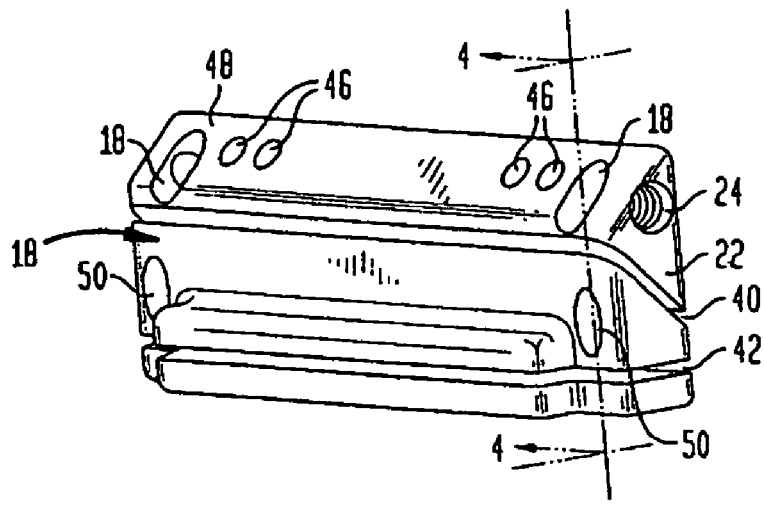
FIG. 3 is a perspective view of the second portion of the cutting block which is adapted to cut the posterior chamfer and posterior bone cuts on the femur.

Referring to FIG. 3, there is shown an enlarged view of the resection block second portion 14 detached from the first portion. Portion 14 includes a pair of cutting guide slots 40, 42 which are adapted to make the posterior chamfer cut and the posterior cut on the distal femur respectively. Portion 14 includes a series of pinholes 46 located adjacent an anterior side 48 of portion 14. Holes 46 are designed to receive bone pins (not shown) which anchor portion 14 to the already resected distal femur after the resection block has been properly located. In addition to pinholes 46 are holes 50 which are adapted to receive medial and lateral mounting pins (not shown).

Figure 4:
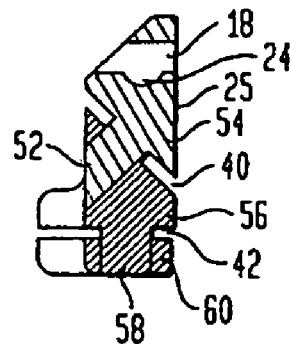
FIG. 4 is a cross-sectional view of the second resection block portion shown in FIG. 3 along lines 4-4.

Referring to FIG. 4, there is shown a cross-sectional view of portion 14 along lines 4-4 of FIG. 3. The cross-section shows the bone contacting proximally facing surface 25, bore 18 including a portion of bore 24 and cutting saw blade slots 40, 42. In addition, FIG. 4 shows a cross-section of pin 52 which couples a top section 54 of portion 14 to a central section 56 thereof. Section 56 includes a pin 58 which, in turn, couples central section 56 to a posterior section 60 which assembly makes up the resection block second portion 14. In the preferred embodiment, pins 52, 58 are located adjacent sides 20, 22 of second portion 14. These pins can be seen in FIGS. 1-3 as extending through the slots of the cutting block. In the preferred embodiment, pins 52, 58 are cylindrical such that a typical oscillating saw blade may be pivoted about each pin when making the required bone cuts. For example, in making the posterior bone cut using slot 42, a saw blade is pivoted about each pin 58 adjacent sides 20, 22 to ensure that the medial and lateral edges of the femur are fully resected. The use of cylindrical pins allow the blade to be inserted from an anterior-lateral or anterior-medial position rather than a purely anterior approach. Obviously, other methods of fabricating second portion 14 are possible, however, pinning three separate segments 54, 56 and 60 together provides a simple and low cost method of manufacturing resection block portion 14.

Figure 5:
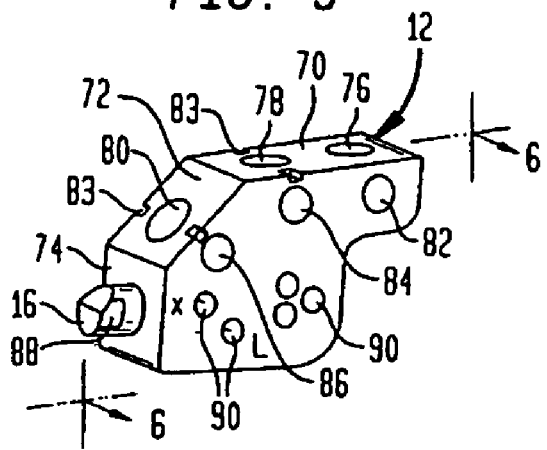
FIG. 5 is a perspective view of the first portion of the resection guide block adapted to be mounted adjacent the lateral side of the distal femur.
Figure 6:
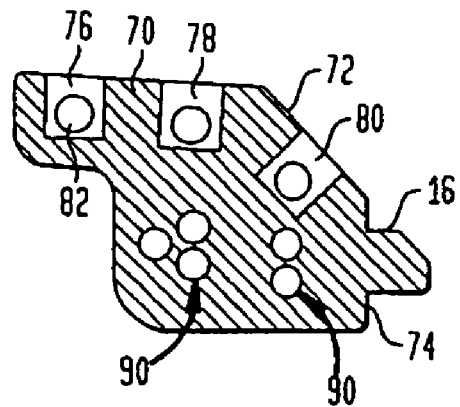
FIG. 6 is a cross-sectional view of the first resection guide block portion of FIG. 5 along lines 6-6.

Referring to FIG. 5, there is respectively shown a perspective view first portion 12 of the resection block. In the preferred embodiment, block 12 includes an anterior surface 70 and a sloping surface 72 which slopes distally from surface 70 towards a distal surface 74. Anterior facing surface 70 includes a pair of blind bores 76, 78. Sloping surface 72 includes a blind bore 80. In the preferred embodiment, bores 76, 78 and 80 are identical in size, i.e. in diameter and in depth. Associated with bores 76, 78 and 80 are set screw bores 82, 84 and 86 respectively. Recesses 83 are provided on opposite sides of bores 78, 80. The function of the bores 76, 78 and 80 and recesses 83 will be discussed in more detail below.

Distally facing surface 74 includes post 16 which, as discussed above, engages bore 18 of second portion 14. Post 16 includes a flat area 88 on which the leading end of a set screw located in each bore 24 can engage to lock the first portion 12 of the resection guide block to second portion 14 in the correct alignment. Also included in portion 12 are a series of bores 90 adapted to receive bone pins (not shown) which fix portion 12 to either the medial or lateral sides of the distal femur once correct alignment is achieved.

Figure 7:
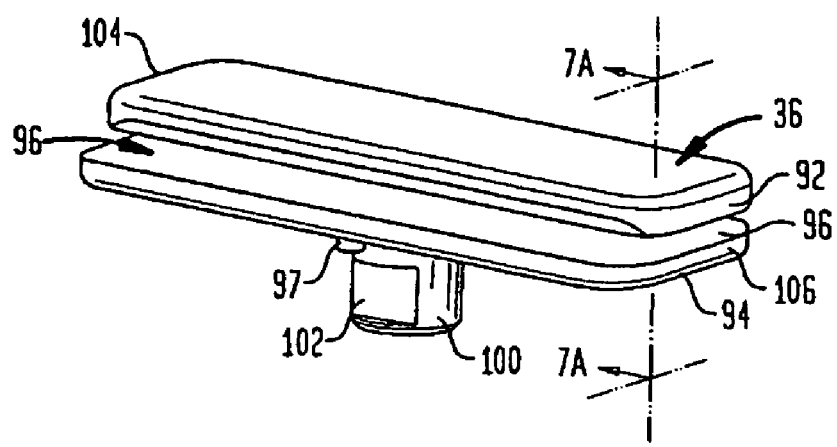
FIG. 7 is an enlarged perspective view of the anterior and anterior chamfer cutting guide adapted for coupling to the resection guide block first portion.
Figure 7A:
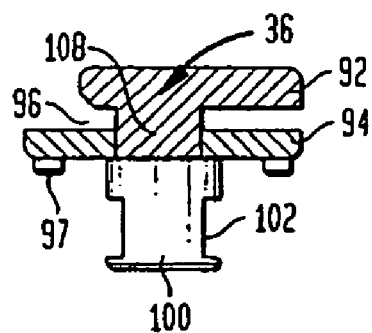

Referring to FIGS. 7 and 7a, there is shown the preferred cutting guide 36 which includes an outer plate portion 92 and an inner plate portion 94 which are spaced to form a cutting guide slot 96 therebetween. Slot 96 is formed by the planar facing surfaces of upper and lower parts 92, 94. Extending outwardly from lower part 94 is a post 100 which, like post 16, has a flat area 102 thereon for engaging the leading end of a set screw. In the preferred embodiment, upper plate 92 and lower plate 94 may be connected by a pair of cylindrical pins 108 located adjacent ends 104, 106 of block 36. Again, a pair of pins 108 adjacent ends 104, 106 is provided so that the oscillating saw blade used to resect the bone can be pivoted therearound to ensure that the entire surface of the bone is resected. In the preferred embodiment, the diameter of post 100 matches the diameter of bores 76 and 78 of first portion 12 of the resection guide block. Cutting guide 36 includes a pair of anti-rotation nubs 97 which engage recess 83 surrounding both bores 76 and 78.

Figure 8:
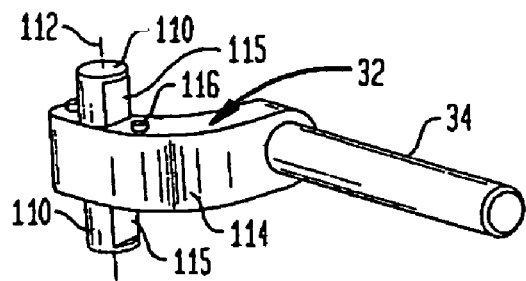
FIG. 8 is a perspective view of the anterior referencing arm which is coupled to the resection guide block first portion.
Figure 9:
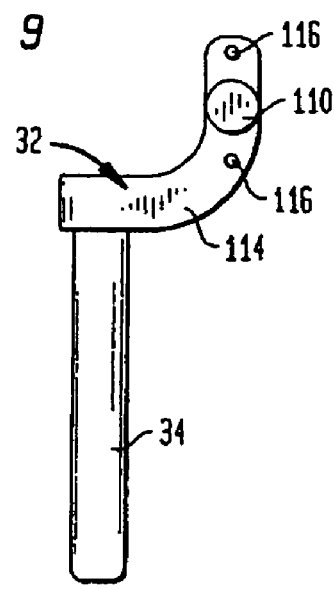
FIG. 9 is a top view of the resection guide arm of FIG. 8.

Referring to FIGS. 8 and 9, there is shown the preferred anterior referencing instrument 32 of system 10 which includes a pair of posts 110 and an arm 34. Posts 110, in the preferred embodiment, are of identical design extend along axis 112 from opposite sides of curved body 114. Posts 110 have a diameter matching the diameter of bore 78 in resection block first portion 12. Posts 110 include flat areas 115 which are designed to be engaged by the leading end of a set screw in bore 84. In addition, posts 110 are surrounded by nubs 116 which are adapted to engage in the recesses 83 located on the sides of bore 78 of portion 12. As with cutting guide 36, the nubs engage the recesses and thereby prevents inadvertent or unwanted rotation between the posts and the bore. By having posts 110 extending from both sides of curved body portion 114, the anterior referencing instrument can be placed in bore 78 with arm 34 in two positions.

Figure 10:
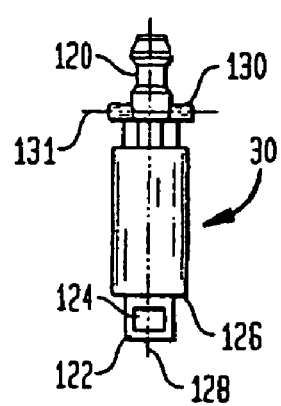
FIG. 10 is a side elevation view of the optical tracker mount which is engageable with the resection guide block first portion.

Referring to FIG. 10, there is shown a preferred adapter 30 which has a first end 120 designed to engage a removable optical tracker (not shown) so that the location of end 120 of adapter 30 can be tracked. Opposite end 120 is a post 122 which has a diameter identical to the diameter of bore 76 and includes a flat surface 124 adapted to engage the leading end of a set screw placed in bore 82 of block portion 12. Adjacent post 122 is a rim 126 having a surface which contacts surface 70 of portion 12. In the preferred embodiment, end 120 of the adapter 30 includes a referencing element 130 which extends along an axis 131 perpendicular to the longitudinal axis 128 of adapter 30. Thus, the distance between axis 131 and surface 126 is known and programmed into the computer-aided navigation system so that once post 122 is mounted in bore 76 the geometric relationships of the parts are known and the spatial location of surfaces 70, 72 and 74 can be determined by the navigation system.

The method of using the multi-piece resection guide system of the present invention starts with the assembly of first portion 12 and second portion 14 to form the resection guide block. How the two parts are assembled depends on whether the block is being used to resect the left or right knee and whether the resection is going to be performed from the lateral or medial side. The assembly of parts 10, 12 would be identical for performing the resection on the left knee from the lateral side or the right knee from the medial side. Conversely, the block would be assembled the same way to perform the resection of the right knee from the lateral side as it would for the resection of the left knee from the medial side. What is important is that when the first portion 12 is placed adjacent the medial or lateral side of the distal femur the second portion 12 extends along and in contact with the already resected distal surface of the femur. As discussed above, in the preferred embodiment, the coupling of portions 12, 14 is accomplished by inserting post 16 into bore 18 and tightening a set screw in bore 24 to engage flat surface 88 and thereby lock the correct position of portions 12, 14. If desired, locating nubs similar to nubs 97, 116 can be used adjacent bore 18 to further prevent rotation of portion 12 with respect to portion 14.

After assembly of the resection guide block, optical tracker adapter 30 is located in bore 76 and anterior referencing guide 32 is located in bore 78 of portion 12. This is accomplished by inserting their respective posts in bores 76, 78 and tightening the respective set screws to lock adapter 30 and referencing guide 32 in position. In the case of guide 32, nubs 116 engage in recesses 83 to further prevent relative rotation of arm 34 with respect to resection block portion 12. As shown in FIG. 1, it should be noted that arm 114 of the anterior referencing guide is curved to avoid contact with adapter 30 place referencing arm 34 at a more proximal position on the distal femur. A modular optical tracker having at least three diodes mounted thereon is then engaged with end 120 of adapter 30. Such an optical tracker is shown in co-pending application Ser. No. 10/768,520. The surgeon then uses the anterior referencing arm 34 to adjust the location of portion 14 and portion 12 of the resection guide block in the anterior/posterior direction on the distal femur. The optical tracker is then used to set the correct internal/external rotational alignment of the assembled resection block. Once the correct positioning is determined, bone pins are inserted through bores 90 on first portion 12 and bores 46 on second portion 14 into the femur to fix the resection guide block in the correct position.

Once the resection guide block is fixed on the distal femur, adapter 30 and anterior referencing guide 32 are removed. Cutting guide 36 is then mounted in bore 78 with nubs 97 engaging recesses 83 and a set screw extending through bore 84 engaging flat area 102 to rigidly clamp the cutting guide 36 to anterior surface 70 of resection guide first portion 12. Once locked in the position, the surgeon uses cutting guide 36 to perform the anterior cut using a powered oscillating saw blade. After the anterior cut is completed, the set screw in bore 84 is loosened and the cutting guide 36 is removed and the post 100 is inserted into bore 80 and surface 72 of portion 12. Again, nubs 97 engage recesses 83 and a set screw in bore 86 is tightened to lock cutting guide 36 in place. The surgeon then makes the anterior chamfer cut with the powered oscillating saw. Once the anterior chamfer cut is made, the surgeon can perform the posterior cut and the posterior chamfer cut in any desired order by using portion 14 of the resection guide block. Again, a powered oscillating saw blade utilizes guide slots 40, 42 to perform these cuts. After all four cuts are made, the bone pins are removed and the entire assembly can be taken off the now fully repaired distal femur. It should be noted that the surgeon can make the cuts in any order but generally the posterior cuts are made after the anterior cuts. When making the posterior cuts the surgeon can angle the saw blade medially or laterally from a plane perpendicular to the resected distal femoral surface and does not have to make the posterior cuts directly from the anterior direction.

Figure 11:
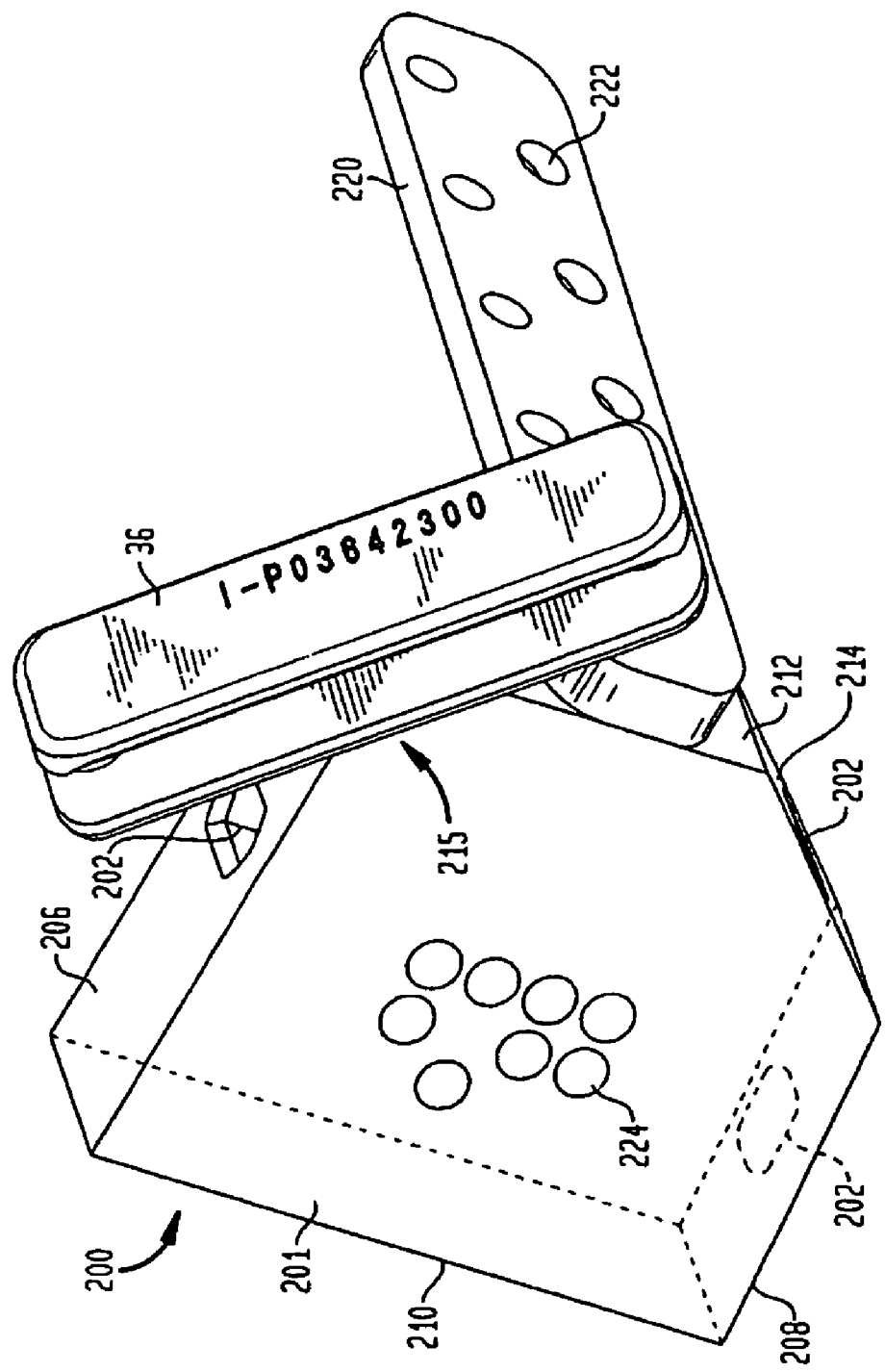
FIG. 11 is an isometric view of an alternate embodiment of the present invention.

Referring to FIG. 11, there is shown an alternate embodiment of the cutting guide system of the present invention generally denoted as 200. The system includes a body portion 201 which includes a series of receptacles 202 for receiving a post 100 of modular cutting guide 36. Block 201 includes an anterior surface 206, a posterior surface 208, a proximally facing surface 210, a distally facing surface 212, and a posterior angled surface 214. The block also has an anterior angled surface 215 which includes a receptacle 202 but which is covered in FIG. 11 by the modular cutting guide 36. Post 100 of modular cutting guide 36 is adapted to engage all of the receptacles 202.

The system 200 includes a mounting arm 220 which has a proximally facing surface adapted to be placed onto a prepared distal surface of the femur. Arm 220 includes a post similar to post 100 to engage receptacle 202 on surface 212 of body 201. Arm 220 includes a series of holes 222 for receiving bone pins which engage either the medial or lateral side of the femur.

Body 201 is positioned in the same manner as first part 12 of the first embodiment described above. It differs, however, since receptacles 202 are placed on surfaces 206, 208, 212, 214 and 215 the modular cutting guide 36 may be positioned on any of these surfaces. Once body 201 is located and mounted on either the medial or lateral side of the femur via pins through holes 50, it would even be possible to place cutting guide 36 on surface 212 to make the distal resection of the femur if such had not already been accomplished by other means as in the preferred method of use. If desired, arm 220 could be replaced by second cutting guide part 14 which can then be used to make the posterior and posterior chamfer cuts. As stated above, modular cutting guide 36 could be located on surfaces 208, 214 to also make the posterior and posterior chamfer cuts without the use of a cutting guide 14. Obviously, in the system 200, the post 100 on modular guide 36, arm 220 and, if utilized, the second part 14 would all be designed to engage receptacles 202.

Figure 12:
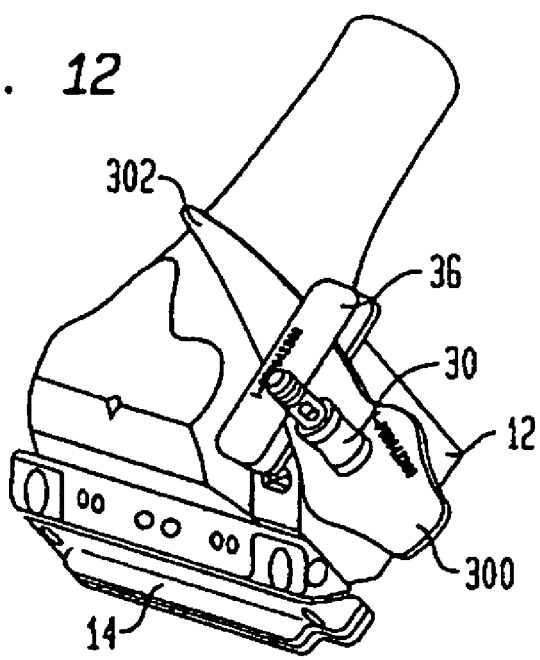
FIG. 12 is an isometric view of the resection guide instruments of the present invention using a plane probe for anterior referencing mounted on the distal femur.
Figure 13:
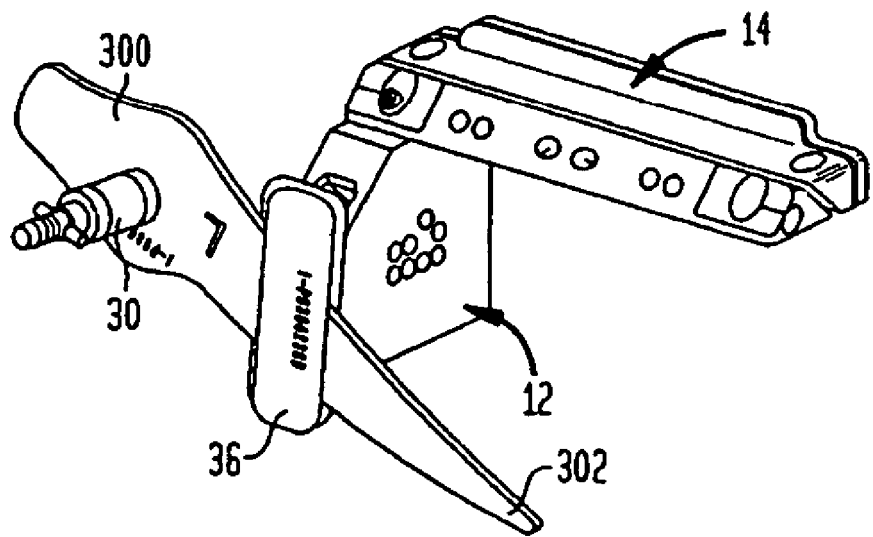
FIG. 13 is an isometric view of the instruments of FIG. 12 removed from the distal femur.

Referring to FIGS. 12 and 13, there is shown yet another embodiment of the distal femoral resection instruments of the present invention.

In the embodiments shown in FIGS. 12 and 13, the anterior referencing guide 32 is replaced with a plane probe 300 which is designed to extend through the modular cutting guide 36 after it has been mounted on the anterior surface 70 of block 12. Thus, modular cutting guide 36 is mounted in bore 76 or 78 which aligns slot 96 with the anterior surface of the femur. Plane probe 300 includes adaptor 30 mounted thereon which can receive an optical tracker (not shown) which, as previously indicated, preferably includes four light emitting diodes so that an optical tracking system can track the orientation of the plane probe 300. In the preferred embodiment, plane probe 300 includes a tip 302 which is adapted to contact the anterior surface of the femur as shown in FIG. 12. Plane probe 300 may be fabricated from thin sheet metal such as titanium sheet, or may be made from a plastic material. In the preferred embodiment, plane probe 300 may be designed for use with a left knee or a right knee, thus requiring a pair of plane probes 300 in any kit supplied. By mounting adaptor 30 on plane probe 300, the adaptor 30 for receiving an optical tracker can be eliminated from portion 12.

Except for the elimination of anterior referencing guide 32, the instrumentation is, in all other respects, the same and includes mounting distal portion 14 on portion 12 in identical manner as described above.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for preparing a distal femur for receiving a prosthetic femoral component comprising:
    resecting a distal surface of a femur to form a planar surface thereon;
    placing a first portion of a resection guide block adjacent either a medial or lateral side of a distal femur, the first portion having an anteriorly facing planar surface when placed adjacent the distal femur the anterior facing surface having a first coupling element extending along an axis generally perpendicular to the anteriorly facing planar surface;
    locating the resection guide block in an anterior/posterior direction by contacting an outermost anterior surface of the distal femur with an anterior referencing arm releasably mounted on the first coupling element of the resection guide block anteriorly facing surface, the resection guide block having a medial-laterally extending second portion mounted on a distal surface of the first portion of the resection guide block extending across the resected planar surface of the distal femur and having a planar surface for contacting the resected planar distal femur surface, the resection guide block second portion including saw guide slots for making a posterior bone cut and a posterior chamfer bone cut;
    orienting the resection guide block in internal/external rotation with respect to longitudinal axis of the femur and thereafter fixedly mounting the guide block on the femur;
    performing an anterior bone cut with a saw blade guided on a cutting guide mounted on the first coupling element after removing the anterior referencing arm mounted on the first coupling element of the anteriorly facing surface of the resection guide block first portion;
    performing the anterior chamfer cut with a saw blade guided on the cutting guide mounted on a second coupling element on a second surface of the resection guide block first portion, the second surface intersecting and forming an obtuse angle with the anteriorly facing planar surface and with the distal surface of the first portion of the resection guide block; and
    performing the posterior and posterior chamfer cuts with a saw blade engaging guide slots in the second portion of the resection guide block.

2. The method as set forth in claim 1 wherein the coupling element on the first portion anteriorly facing and second surfaces is a bore and the cutting guide has a peg extending therefrom for insertion into the bore formed in the first portion anteriorly facing and second surfaces.

3. The method as set forth in claim 1 wherein the first portion of the resection guide has a distally extending coupling element and the second portion has first and second ends each with a coupling element engageable with the first portion coupling element wherein coupling the first portion with the second portion first end forms a resection guide block for a right knee from the medial side or the lateral side of the femur and engaging the second end of the second portion with the first portion coupling forms a cutting block for a left knee from a medial side or a lateral side of a right knee.

4. The method as set forth in claim 1 wherein the resection guide block is oriented in internal/external rotation on the lateral side of the femur by aligning the guide block with respect to the distal femur with an optical tracker.

5. The method as set forth in claim 4 wherein a modular optical tracker is mounted on the first resection guide portion and is removed prior to making the anterior bone cut with the cutting guide.

6. The method as set forth in claim 5 wherein the modular optical tracker is mounted on the anteriorly facing surface of the first portion.

7. The method as set forth in claim 1 wherein the mounting of the resection guide block includes pinning the first portion of the resection block to the lateral femur after setting the anterior/posterior location and the internal/external rotation.

8. The method as set forth in claim 7 wherein the mounting of the resection guide block includes pinning the second portion of the resection guide block to the distal femur.

9. The method as set forth in claim 1 wherein the anterior chamfer bone cut is made with the modular slotted cutting guide placed on the second surface on the first portion of the resection guide which second surface slopes distally in the anterior to posterior direction.

10. A method for preparing a distal femur for receiving a prosthetic femoral component comprising:
    resecting a distal surface of a distal femur to form a planar surface thereon;
    placing a block having a distally facing surface with a medially-laterally extending arm thereon, the arm having a planar proximally facing surface extending across the resected distal surface of the femur, adjacent either a medial or lateral surface of the resected distal femur;
    placing a removable anterior referencing arm on a coupling element formed on planar anteriorly facing surface of the block, the coupling element extending along an axis generally perpendicular to the planar anteriorly facing surface of the block and positioning the block in an anterior-posterior direction with respect to the distal femur by contacting an anterior outermost surface of the distal femur with the anterior referencing arm;
    positioning the block in a proximal-distal direction in the distal femur by placing the medially-laterally extending arm proximally facing planar surface against the planar distal femur surface;
    removing the anterior referencing arm from the block; and
    resecting posterior condyles of the distal femur with a saw guide surface on the medially-laterally extending arm and resecting anterior condyles of the distal femur by making two resections with a single removable cutting guide mounted on the coupling element formed on the anterior surface of the block and on a second coupling element formed on a planar block surface extending from the anteriorly facing surface to the distal facing surface at an obtuse angle to both the anteriorly facing and distally facing surfaces.

11. The method as set forth in claim 10 wherein the block has an angled surface extending between the anteriorly facing surface thereof and the medially-laterally extending arm and wherein an anterior angled surface is formed on the distal femur using the angled block surface to guide a saw blade.

12. The method as set forth in claim 11 further comprising coupling a modular bone resection guide in series to the anteriorly facing surface and the anterior angled surface for guiding the saw blade.

13. The method as set forth in claim 12 wherein the modular anterior referencing arm located on the anteriorly facing surface is removed prior to placing the cutting guide on the anteriorly facing surface.

14. The method as set forth in claim 10 wherein the medially-laterally extending arm has two saw guide surfaces, a guide first surface for performing a posterior condyle resection and a second surface for making a posterior chamfer resection on the distal femur.

* * * * *